United States Patent [19]
Littrell et al.

[11] Patent Number: 5,137,519
[45] Date of Patent: Aug. 11, 1992

[54] CATHETER RETENTION COLLAR AND SUPPORT

[75] Inventors: Perry K. Littrell; Wendy G. Van Dusen, both of Miami Lakes, Fla.

[73] Assignee: Cordis Corporation, Miami Lakes, Fla.

[21] Appl. No.: 491,961

[22] Filed: Mar. 12, 1990

[51] Int. Cl.⁵ .............................................. A61M 5/32
[52] U.S. Cl. .................................................. 604/174
[58] Field of Search ............... 604/180, 179, 178, 177, 604/176, 174, 158, 164, 116, 117; 128/DIG. 6, DIG. 26

[56] References Cited

U.S. PATENT DOCUMENTS

| | | | |
|---|---|---|---|
| 978,708 | 12/1910 | Dean | 604/174 X |
| 2,008,340 | 7/1935 | Salvati et al. | 604/174 |
| 2,266,230 | 12/1941 | Mazzeo et al. | 604/174 X |
| 2,266,231 | 12/1941 | Mazzeo et al. | 604/174 X |
| 2,402,306 | 6/1946 | Turkel | 604/174 |
| 3,288,137 | 11/1966 | Lund | 604/180 X |
| 3,782,388 | 1/1974 | Page | |
| 3,856,020 | 12/1974 | Kovac | |
| 4,212,297 | 7/1980 | Johnson, Jr. et al. | 604/174 X |
| 4,224,937 | 9/1980 | Gordon | |
| 4,250,880 | 2/1981 | Gordon | |
| 4,632,670 | 12/1986 | Mueller, Jr. | |
| 4,682,978 | 7/1987 | Martin | |
| 4,711,636 | 12/1987 | Bierman | |
| 4,769,010 | 9/1988 | Fenton, Jr. et al. | |
| 4,863,432 | 9/1989 | Kvalo | |

Primary Examiner—John J. Wilson
Assistant Examiner—Jeffrey A. Smith
Attorney, Agent, or Firm—Gerstman & Ellis, Ltd.

[57] ABSTRACT

A catheter retention collar for retaining a catheter on the skin of a patient in a desired position. The collar comprises a tubular member defining a bore for receiving and retaining a catheter therein. The tubular member defines a laterally projecting apertured member to facilitate securance of the retention collar to the skin. The apertured member may engage a pivot rod in pivoting relation therewith, with the pivot rod being carried on one side of a generally flat platform member, the other side of the platform member being adhesive-coated to permit adhesion to the skin of a patient.

9 Claims, 1 Drawing Sheet

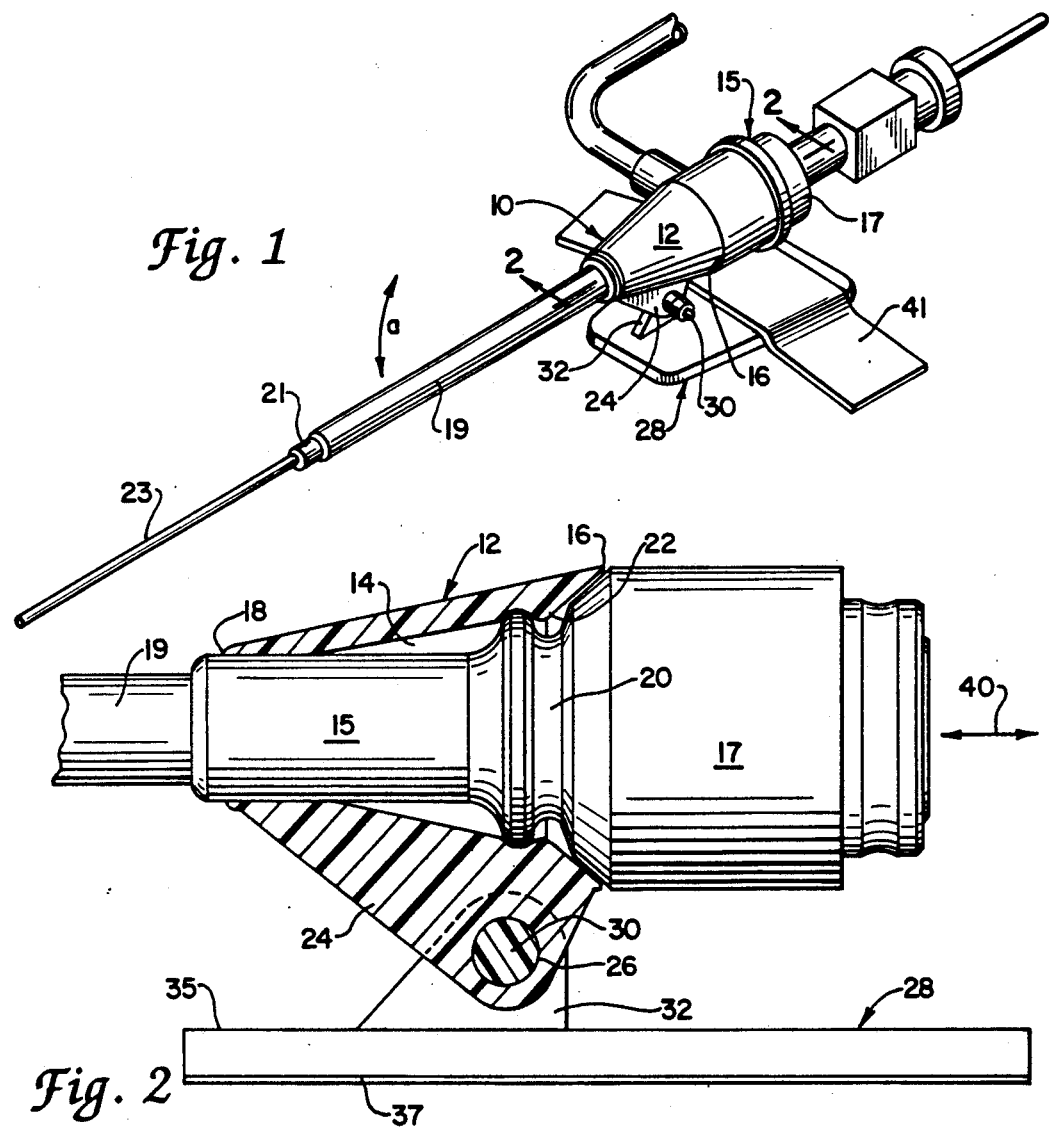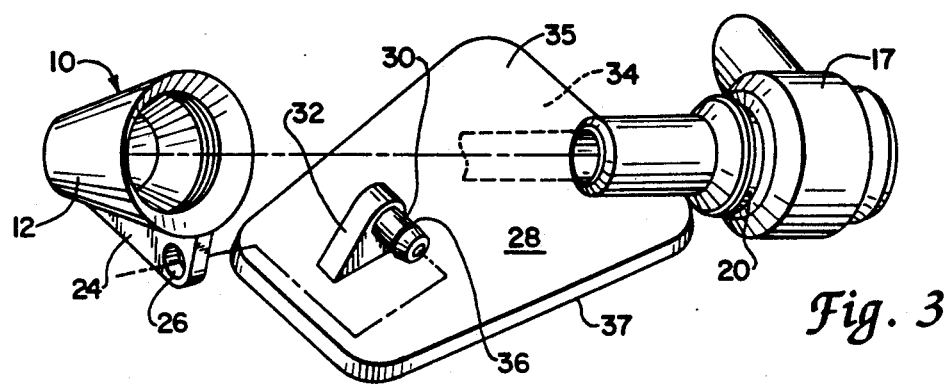

CATHETER RETENTION COLLAR AND SUPPORT

BACKGROUND OF THE INVENTION

Catheters such as those for access to the arteriovenous system of a patient have often been merely taped to the skin of the patient to hold them in position. However, this has the disadvantage that the catheter cannot be conveniently adjusted either by rotation about its own axis, or by elevation upwardly or downwardly in a varying angle transverse to the skin. Thus, such catheters may be somewhat painful, and damaging to tissue at their entry sites, because they are not positioned in optimal manner.

In attempts to improve the problem of securing catheters to the skin, winged catheter assemblies have been provided of various kinds, for example as shown in Kvalo U.S. Pat. No. 4,863,432. Other catheter or needle anchoring devices are provided in which attempts are made to permit change of the angularity of the catheter with respect to the skin, for example U.S. Pat. Nos. 3,288,137; 4,769,010; 4,250,880; and 4,224,937. In these patents, attempts are made to provide some vertical angular adjustability to needles or catheters which extend through the skin, but the mode of adjustment is relatively difficult, and the structures used are fairly complex and cumbersome.

By this present invention a simple, inexpensive catheter retention collar is provided for retaining a catheter on the skin of a patient in desired position. The collar may either be sutured to the skin, or it may be used in conjunction with a flat member which adheres to the skin, to provide easy rotational and vertical angular adjustability to the catheter in its relation to the skin, while still providing firm retention of the catheter in desired position. Optionally the adjustability can be essentially spontaneous, so that pressures of the catheter against the tissue at the skin entry site are minimized, contrary to the prior art.

DESCRIPTION OF THE INVENTION

In this invention a catheter retention collar is provided for retaining a catheter on the skin of a patient in a desired position. The retention collar comprises a tubular collar defining a bore for receiving and retaining a catheter therein. The tubular collar defines a laterally projecting aperture member to facilitate securance of the collar to the skin.

The laterally projecting aperture member may be directly sutured to the skin by passing the sutures through the aperture or apertures of the member, so that simple, inexpensive, and effective catheter retention may be provided, which still permits rotation, advancement, and retraction of the catheter. This arrangement also provides a relatively loose attachment of the catheter collar, which can rotate about the sutures to a certain extent, so that the angular relation of the catheter to the skin can spontaneously adjust, to minimize stress at the skin entry site.

Alternatively, the laterally projecting aperture member may define an aperture which receives a pivot rod in pivoting relation therewith, with the aperture member typically pivoting about the stationary rod.

The pivot rod is carried on one side of a generally flat platform member, which may preferably be rigid or semi-rigid, but may be flexible if desired. An opposed side of the flat member is adhesive-coated, to permit adhesion to the skin of a patient. Thus, the catheter retention collar is held on the skin of the patient in pivoting relation, preferably vertical pivoting relative to the generally flat member.

Hence, a catheter carried in the collar is provided with substantial degrees of freedom in that it can be rotated about its own axis, longitudinally advanced and retracted, and also pivoted with the retention collar relative to the skin, for reduction of stress at the skin entry site. At the same time, the retention collar and any catheter carried therein is firmly retained adjacent the skin by the adhesion of the generally flat member.

The term "catheter" is understood to include catheter sheath introducers, which are a type of catheter used to provide initial access to an artery, for example, and to permit the advancement of other catheters into the artery while minimizing bleeding. Additionally, the catheter retention collar and pivotally attached, generally flat member may be used in conjunction with any desired type of tubular access member.

Preferably, the bore of the retention collar of this invention defines an annular, snap-fit rib which is proportioned to engage a suture groove of a catheter hub, to retain the catheter hub in releasably-locked relation with the collar. For example, the snap-fit rib may engage the suture groove of the hub of a commercially available catheter sheath introducer, to keep the introducer in desired position with respect to the artery into which it extends.

Also, it is generally preferred for the bore of the retention collar to define a generally tapering diameter from one end to the other. The above-described snap-fit rib may be positioned adjacent the larger-diameter end of the bore.

The aperture of the tubular collar and the pivot rod that it receives may also be releasably locked together in snap-fit relation.

Thus, a catheter retention system is provided which exhibits great versatility, since the catheter is firmly retained, but in a freely pivoting relation which is not found in prior art systems. Thus, adjustments that must be made can typically be done spontaneously. Also, the system of this invention simplifies the installation of catheters.

DESCRIPTION OF THE DRAWINGS

FIG. 1 is a perspective view of the catheter retention collar and support of this invention, carrying a conventional catheter introducer system;

FIG. 2 is a fragmentary sectional view taken along line 2—2 of FIG. 1; and

FIG. 3 is a fragmentary, exploded perspective view of the catheter retention collar and support of this invention, also including a fragment of the catheter introducer.

DESCRIPTION OF SPECIFIC EMBODIMENTS

Referring to the drawings, catheter retention collar 10 is shown to define a tubular member 12 having a bore 14 for receiving and retaining a catheter therein, which specifically may be a conventional catheter sheath introducer 15. Specifically from FIG. 2 the shape of the bore can be seen to be of a generally tapering diameter from end 16 to end 18.

Catheter sheath introducer 15 defines a hub 17 having a conventional suturing groove 20, into which snap-fit rib 22 of tubular member collar 12 can fit. As shown, annular rib 22 is positioned near the end of member 12 at which the bore diameter is maximum. Thus, catheter sheath introducer 15 may be firmly but releasably retained to retention collar 10. Hub 17 of catheter introducer 15 carries, as is conventional, a distal outer tubular portion 19, through which various catheters 21 and guide wires 23 can project, to provide access by means of various conventional procedures to the cardiovascular system of a patient.

Retention collar 10 also defines a laterally projecting member 24 which defines an aperture 26, and is preferably integral with tubular member 12 as a single, molded piece. This permits retention collar 10 to be pivotally attached to a flat plate 28, which is typically made of semi-flexible plastic, by means of pivot rod 30, which is attached to post 32 in perpendicular relation. Post 32, in turn, may be an integral part of plate 28. The side 34 of plate 28 which is opposed to the side 35 that carries pivot 30 and post 32 may preferably carry a layer of adhesive 37 suitable for skin adhesion. If desired, reinforcing adhesive tape 41 may provide added securance of plate 28 to the skin.

Accordingly, as shown in FIG. 1 an assembled structure of catheter retention collar 10 and plate member 28 may be locked together in pivotal relation, with pivot rod 30 residing within aperture 26 and held there in a snap fit relation provided by annular snap rib 36. Thus, when plate 28 is attached on its adhesive side 34 to the skin of a patient, catheter sheath introducer 15 may also be retained in pivotal relation to plate 28 when it extends through retention collar 10.

Catheter introducer 15 may be advanced until it locks in snap-fit relation with collar 10, but it can always be retracted as desired. Additionally, it can be seen that catheter introducer 15 may be rotated about its own axis 40 as desired, and it may rotate with retention collar 12 in pivotal motion about pivot rod 30, to provide an adjustable vertical angle to at least that portion of the catheter introducer 15 which is outside of the skin, to reduce stresses on the tissue, and to easily and even spontaneously position the catheter at the optimum vertical angle a.

Plate 28 may be of trapezoidal shape as shown in FIG. 3, for improved fitting and adhesion on the skin. Plate 28 may be integrally molded out of plastic along with post 32 and pivot rod 30. Retention collar 10 is also capable of one-piece, integral molding so that the two components, catheter retention collar 10 and platform or plate 28, can be manufactured on a large volume basis at very low cost.

The above has been offered for illustrative purposes only, and is not intended to limit the scope of the invention of this application, which is as defined in the claims below.

That which is claimed is:

1. A catheter retention device for retaining a catheter on the skin of a patient in a desired position, which comprises:

rotational retention means for rotatably holding the catheter and for permitting the catheter to rotate generally about the longitudinal axis of said catheter, said rotational retention means comprising a tubular member defining a bore, said bore defining an annular, snap-fit rib proportioned to engage a suture grove of a catheter hub, to retain the catheter hub in releasably-locked relation with said tubular member;

said rotational retention means having pivot means for permitting the catheter also to pivot about an axis that is generally perpendicular to said longitudinal axis; and means for securing said retention means to the skin of a patient.

2. The catheter retention device of claim 1 in which said bore defines a generally tapering diameter, said snap-fit rib being positioned adjacent the larger-diameter end of said bore.

3. The catheter retention device of claim 1 in which pivot means includes an aperture proportioned to receive a pivot rod.

4. The catheter retention device of claim 3 in which said aperture carries a pivot rod in pivoting relation therewith.

5. The catheter retention device of claim 4 in which said aperture and pivot rod are releasably locked together in snap-fit relation.

6. A catheter retention device as defined by claim 1, said securing means comprising a generally flat platform member having a top side and a bottom side, said bottom side carrying adhesive to permit adhesion to a skin of a patient.

7. The catheter retention device of claim 6 in which the platform member is of substantially the shape of a trapezoid.

8. A catheter retention device for retaining a catheter on the skin of a patient in a desired position, which comprises:

a tubular member defining a bore for rotatably holding the catheter and for permitting the catheter to rotate generally about the longitudinal axis of said catheter, said bore defining an annular snap-fit rib proportioned to engage a suture groove of a catheter hub, to retain the catheter hub in releasably-locked relation with said tubular member;

said rotational retention means having pivot means for permitting the catheter also to pivot about an axis that is generally perpendicular to said longitudinal axis; and means for securing said retention means to the skin of a patient.

9. A catheter retention device as defined by claim 8, said securing means comprising a generally flat platform member having a top side and a bottom side, said top side carrying a pivot rod and said rotational retention means defining an aperture for receiving said pivot rod.

* * * * *